United States Patent [19]
Yoshimoto et al.

[11] Patent Number: 4,708,796
[45] Date of Patent: Nov. 24, 1987

[54] MATERIAL TRANSFER APPARATUS OF HOLLOW FIBER TYPE

[75] Inventors: Masayuki Yoshimoto, Toyoake; Toshiaki Takagi, Fujinomiya, both of Japan

[73] Assignee: Terumo Kabushiki Kaisha (Terumo Corporation), Tokyo, Japan

[21] Appl. No.: 781,138

[22] Filed: Sep. 27, 1985

[30] Foreign Application Priority Data

Sep. 29, 1984 [JP] Japan .................. 59-148205[U]

[51] Int. Cl.[4] ............................................. B01D 13/01
[52] U.S. Cl. ................................. 210/321.8; 422/48
[58] Field of Search ............... 210/321.2, 321.3, 321.4, 210/323.2; 422/48

[56] References Cited

U.S. PATENT DOCUMENTS

| | | | |
|---|---|---|---|
| 4,201,673 | 5/1980 | Kanno et al. | 210/323.2 |
| 4,218,313 | 8/1980 | Aid et al. | 210/321.3 |
| 4,237,013 | 12/1980 | Yamazaki et al. | 210/321.2 |
| 4,283,284 | 8/1981 | Schnell | 210/321.3 |
| 4,334,993 | 6/1982 | Norton | 210/321.3 |
| 4,374,802 | 2/1983 | Fukasawa | 422/48 |

FOREIGN PATENT DOCUMENTS

| | | |
|---|---|---|
| 0031620 | 7/1981 | European Pat. Off. . |
| 0058275 | 8/1982 | European Pat. Off. . |
| 2330429 | 6/1977 | France . |
| 2524379 | 10/1983 | France . |
| 2053725 | 2/1981 | United Kingdom . |

OTHER PUBLICATIONS

Research Disclosure, No. 225, Jan. 1983, p. 9, No. 22528, Havant Hampshire, GB: "Hollow Fiber Dialyzer".

*Primary Examiner*—Ivars Cintins
*Attorney, Agent, or Firm*—Cushman, Darby & Cushman

[57] ABSTRACT

A material transfer apparatus of hollow fiber type is provided comprising tubular housing, a bundle of a plurality of hollow fiber membranes axially extending through the housing, a first fluid chamber defined by the outer surface of the hollow fibers and the inner surface of the housing, a first fluid inlet and a first fluid outlet both in fluid communication with the first chamber for passing a dialysate into and out of the first chamber, partitions supporting the opposite ends of the hollow fibers and isolating the fiber end from the first chamber, and a second fluid inlet and a second fluid outlet both in fluid communication with the interior space of the hollow fibers for passing a blood into and out of the fiber interior space. Flowpath forming members each having an elastomeric annular member integrally molded thereto are mounted on opposite ends of the housing. The elastomeric member is secured in pressure contact to the partition to provide a fluid-tight seal between the partition and the flowpath member.

9 Claims, 6 Drawing Figures

PRIOR ART

MATERIAL TRANSFER APPARATUS OF HOLLOW FIBER TYPE

BACKGROUND OF THE INVENTION

This invention relates to a material transfer apparatus of hollow fiber type, and more particularly to a medical material transfer apparatus of hollow fiber type such as a dialyzer or oxygenator.

Hollow fiber type material transfer apparatus are well known in the art. One known dialyzer includes a tubular housing and a bundle of a plurality of hollow fibers axially extending through the housing and each presenting a material exchange membrane. A dialysate chamber is defined by the outer surface of the hollow fibers and the inner surface of the housing, a dialysate inlet and a dialysate outlet are both in fluid communication with the dialysate chamber. Partitions support the opposite ends of the hollow fibers and isolate the fiber end from the dialysate chamber. A blood inlet and a blood outlet are both in fluid communication with the interior space of the hollow fibers.

Hollow fiber oxygenators are shown in U.S. Pat. Nos. 4,239,729 and 4,376,095. Such a hollow fiber oxygenator includes a tubular housing and a bundle of a plurality of hollow fibers axially extending through the housing and each presenting an oxygen permeable membrane. An oxygen or blood chamber is defined by the outer surface of the hollow fibers and the inner surface of the housing, an oxygen or blood inlet and an oxygen or blood outlet are both in fluid communication with the oxygen or blood chamber. Partitions support the opposite ends of the hollow fibers and isolate the fiber end from the oxygen or blood chamber. A blood or oxygen inlet and a blood or oxygen outlet are both in fluid communication with the interior space of the hollow fibers.

In these material transfer apparatus of hollow fiber type, a flowpath forming member in the form of a header provides a fluid inlet or outlet for passing a material transfer fluid into and out of the fiber interior space. The term material transfer fluid used herein includes both a fluid to be treated and a treating fluid between which a certain material is transferred. The headers are fixedly secured to the opposite ends of the housing.

Prior art headers are generally provided with various sealing structures for preventing fluid leakage from the housing as shown in FIGS. 4 to 6. The sealing structures and their drawbacks are described below.

Referring to FIG. 4, the header includes three elements, a flowpath forming member 20 having a fluid inlet 200, an attachment cover 30, and an O-ring 35. When the attachment cover 30 is threadably engaged and fastened to one end of the housing 1, the O-ring 35 is secured in pressure contact to a partition 40 to provide a fluid-tight seal between the flowpath forming member 20 and the partition 40. The flowpath forming member 20 at the inner surface is formed with an annular groove to receive the O-ring 35 therein preventing movement of the O-ring.

However, blood often leaked at the joint between the flowpath forming member 20 and the partition 40 when the O-ring was not properly set in the groove or when once set-in O-ring came out of the groove during the assembly. Further, since the header included three elements, the material cost was high and the production process was complicated.

FIG. 5, illustrates a header of a one-piece member. the flowpath forming member 20 has an attachment portion 204 threaded at its flared end. When this attachment portion 204 is threadably engaged and fastened to the end of the housing 1, a tongue 206 on the inner surface of the flowpath forming member 20 is brought in pressure contact to the partition 40 to provide a primary seal. A sealant 37 is then potted through a gate 208 into a gap where it is cured to provide a secondary seal.

In this header, it is the tongue 206 in biting engagement with the partition 40 that provides a fluid-tight seal between the flowpath forming member 20 and the partition 40. However, if this seal is insufficient, the subsequently introduced sealand could flow beyond the tongue 206 over the central portion of the partition 40 to block the hollow fibers. Further, this system required a step of potting a sealant which took a quite long time until curing.

FIG. 6, illustrates another header which is similar to the previously described header shown in FIG. 4 except that the thread attachment portion 204 is continuously formed at an end of the flowpath forming member 20. The O-ring 35 is retained to provide a fluid tight seal. Although less elements are used than in the header of FIG. 4, the header of FIG. 6 had similar drawbacks as pointed out for the header for FIG. 4.

SUMMARY OF THE INVENTION

It is, therefore, an object of the present invention to provide an improved material transfer apparatus of hollow fiber type which has eliminated the above-mentioned drawbacks, and provides a reliable fluid-tight seal as well as high mass productivity.

According to the present invention there is provided a material transfer apparatus of hollow fiber type for transferring a certain material between first and second fluids, comprising a tubular housing, a bundle of a plurality of hollow fiber membranes axially extending through the housing and allowing the material to migrate thereacross, a first fluid chamber defined by the outer surface of said hollow fibers and the inner surface of said housing, a first fluid inlet and a first fluid outlet both provided on the housing in fluid communication with said first fluid chamber for passing the first material transfer fluid into and out of the first chamber, partitions supporting the opposite ends of said hollow fibers and isolating the fiber ends from said first fluid chamber, and a second fluid inlet and a second fluid outlet both in fluid communication with the interior space of said hollow fibers for passing the second material transfer fluid into and out of the fiber interior space, characterized in that a first flowpath forming member having the second fluid inlet is mounted on one end of the housing, a second flowpath forming member having the second fluid outlet is mounted on the other end of the housing, and an elastomeric annular member is integrally molded to each said flowpath forming members on its inner surface, wherein the elastomeric member is secured in pressure contact to the partition by the flowpath forming member to provide a fluid-tight seal between the partition and the flowpath forming member.

Several preferred embodiments of the present invention are described below.

(i) The elastomeric annular member is in contact with a peripheral portion of the partition that surrounds the hollow fiber bundle.

(ii) The first flowpath forming member includes a leading portion of a reduced diameter to form the second fluid inlet, an intermediate portion continuously extending and dilating from the inner surface of the fluid inlet to define a flowpath for distributing the second fluid substantially over the partition, and an attachment portion continuously extending from the intermediate portion and adapted to be attached to one end of the housing. A first elastomeric annular member is joined to the flowpath forming member near the boundary between the intermediate and the attachment portions. The second flowpath forming member includes a leading portion of a reduced diameter to form the second fluid outlet, an intermediate portion continuously extending and dilating from the inner surface of the fluid outlet to define a flowpath for collecting the second fluid, and an attachment portion continuously extending from the intermediate portion and adapted to be attached to the other end of the housing. A second elastomeric annular member is joined to the flowpath forming member near the boundary between the intermediate and the attachment portions.

(iii) The elastomeric annular member is in full contact with the inner boundary surfaces of the intermediate and attachment portions of the flowpath forming member.

(iv) An annular space is defined between the elastomeric annular member and the inner surface of the attachment portion of the flowpath forming member.

(v) The attachment portion of the flowpath forming member is electronically heat sealed to the housing end.

(vi) The flowpath forming member and the elastomeric annular member are integrally molded by two-color injection molding.

(vii) The flowpath forming member is molded from a polyolefin and the elastomeric annular member is molded from a polyolefin elastomer.

(viii) The material transfer apparatus constitutes a dialyzer.

BRIEF DESCRIPTION OF THE DRAWINGS

These and other objects, features, and advantages of the present invention will be readily understood from the following description taken in conjunction with the accompanying drawings, in which.

DESCRIPTION OF THE PREFERRED EMBODIMENTS

Figure 1:
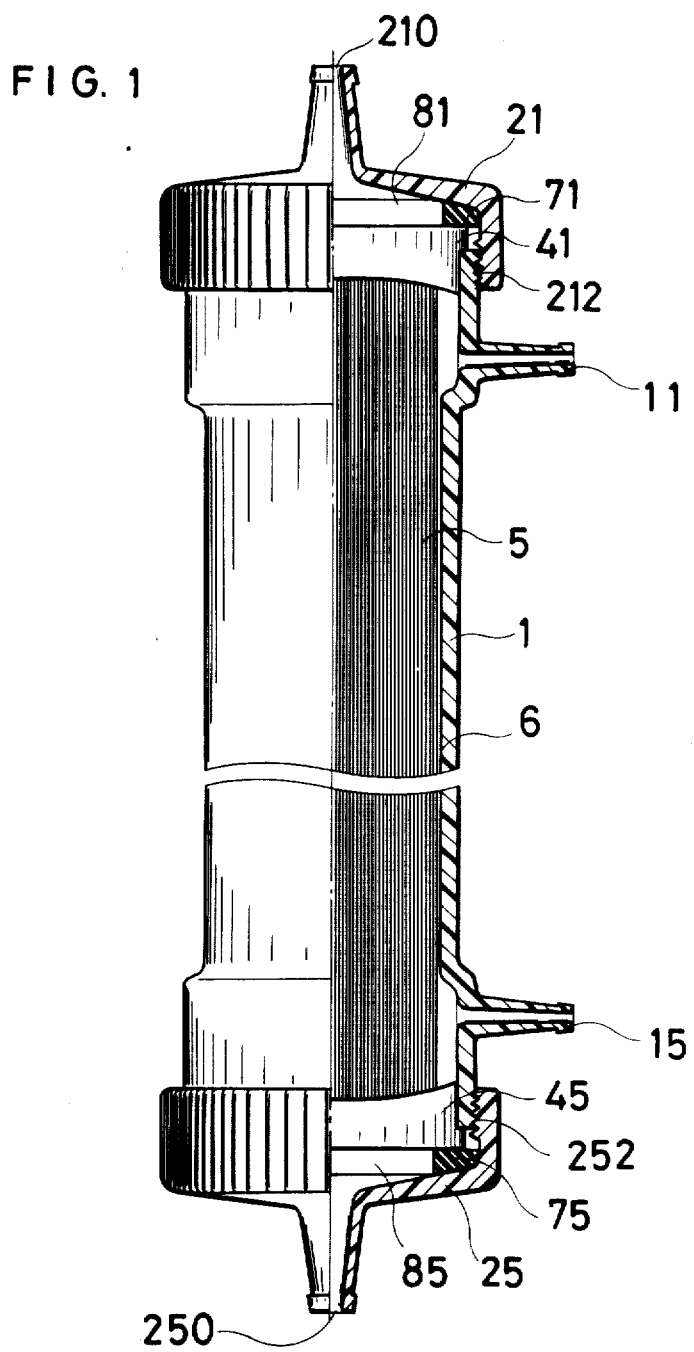
FIG. 1 is an elevation, with the first half in cross section, of a material transfer apparatus of hollow fiber type according to one embodiment of the present invention.

Referring to FIG. 1, there is schematically illustrated an artificial kidney or dialyzer of hollow fiber type according to one preferred embodiment of the material transfer apparatus of the present invention. The dialyzer includes a cylindrical housing 1 which receives a bundle of 5,000 to 10,000 hollow fibers 5 each presenting a membrane allowing a certain material to migrate thereacross and extending axially through the housing in mutually spaced-apart relationship. The opposite ends of the hollow fibers 5 are fluid tightly engaged and retained by partitions 41 and 45 fitted in the housing 1 at its opposite ends. The hollow fibers extend throughout the partition and preferably terminate at the outer surface thereof without blockage in the opening of fibers. For brevity of description, the partitions 41, 45 and the corresponding housing ends are referred to as first and lower partitions and upper and lower housing ends. It should be understood that the terms upper and lower need not necessarily correspond to the actual positions of these members during operation of the apparatus.

Examples of the hollow fiber membranes 5 used in the dialyzer include cellulose membranes regenerated by cuprammonium process or cellulose acetate process, stereo-complex membranes of polymethyl methacrylate, polyacrylonitrile membranes, ethylene-vinyl alcohol copolymer membrane, etc.

Upper or first and lower or second flowpath forming members 21 and 25 are fixedly secured to the opposite ends of the housing 1, respectively.

The inner surfaces of the partitions 41, 45, the inner wall of the housing 1, the outer wall of the hollow fibers 5 define a first fluid chamber 6 in the form of a dialysate chamber. The housing 1 is provided near its upper and lower ends with a first fluid inlet in the form of a dialysate inlet 11 and a first fluid outlet in the form of a dialysate outlet 15 both in fluid communication with the first fluid chamber 6 for passing a first material transfer fluid or dyalysate into and out of the first chamber.

The inner surface of the first flowpath forming member 21 and the outer surface of the upper partition 41 defines a second fluid incoming chamber in the form of a blood incoming chamber 81 in fluid communication with the interior space of each hollow fiber 5. The flowpath forming member 21 has at its apex a second fluid inlet in the form of a blood inlet 210 for passing a second material transfer fluid or blood into the chamber 81 and then the fiber interior space.

The inner surface of the second flowpath forming member 25 and the outer surface of the lower partition 45 define a second fluid outgoing chamber in the form of a blood outgoing chamber 85 in fluid communication with the interior space of each hollow fiber 5. The flowpath forming member 25 has at its apex a second fluid outlet in the form of a blood outlet 250 for passing the second material transfer fluid or blood out of the fiber interior space.

The partitions 41 and 45 serve for the important function of isolating the interior from the exterior of the hollow fibers 5, that is, isolating the second chamber or blood passage from the first chamber 6. In general, the partitions 41 and 45 are formed by casting a polar, high molecular weight potting agent, for example, polyurethane, silicone, and epoxy resins to the inner wall of the housing by the centrifugal casting process where it is cured.

Figure 2:
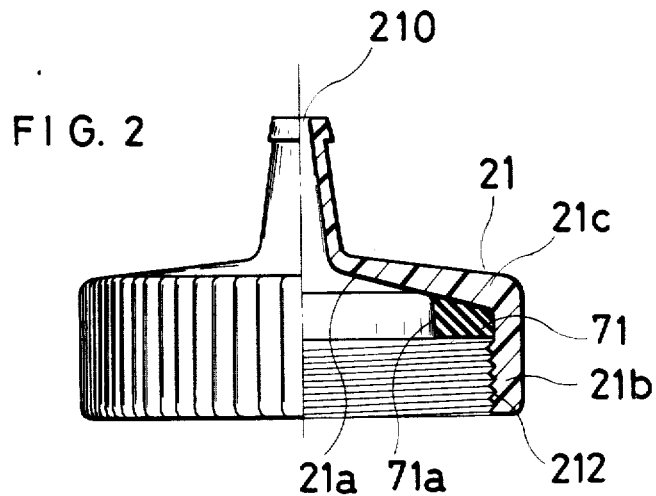
FIG. 2 is a partially cut-away elevation of a flowpath forming member with an elastomeric annular member used in the material transfer apparatus in FIG. 1.
Figure 3:
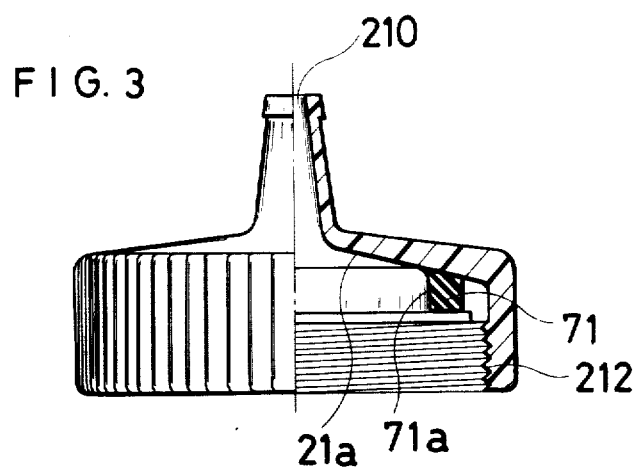
FIG. 3 is a partially cut-away elevation of another example of the flowpath forming member.

FIGS. 2 and 3 illustrate different examples of a flowpath forming member/elastomeric annular member assembly of the present invention.

The flowpath forming member 21 includes a leading portion of a reduced diameter to form the second fluid inlet 210, an intermediate portion 21a continuously extending and dilating from the inner surface of the second fluid inlet 210 to define a flowpath for distributing the second fluid from the fluid inlet 210 substantially over partition 41, and an attachment portion 21b axially extending from the intermediate portion in an opposite direction to the fluid inlet 210 and adapted to be attached to the housing end.

Figure 4:
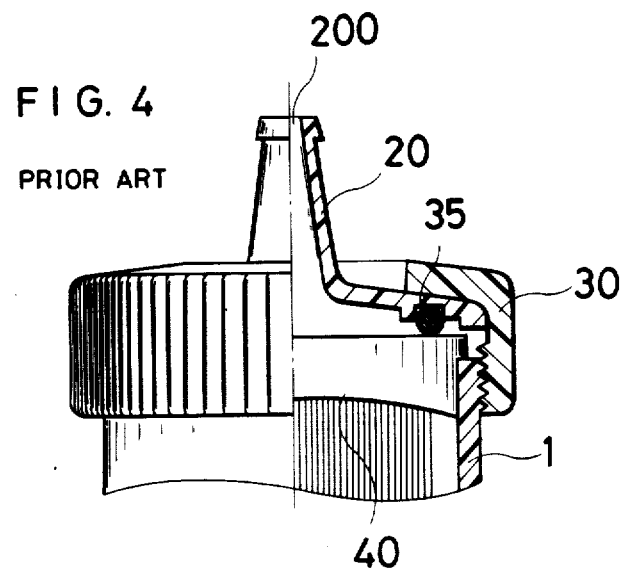
FIGS. 4 to 6 are partially cut-away elevations of flowpath forming members in conventional material transfer apparatus.
Figure 5:
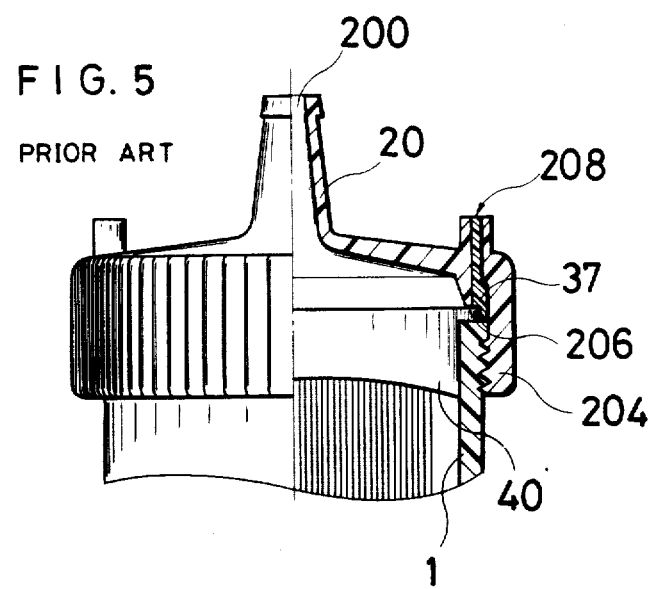
Figure 6:
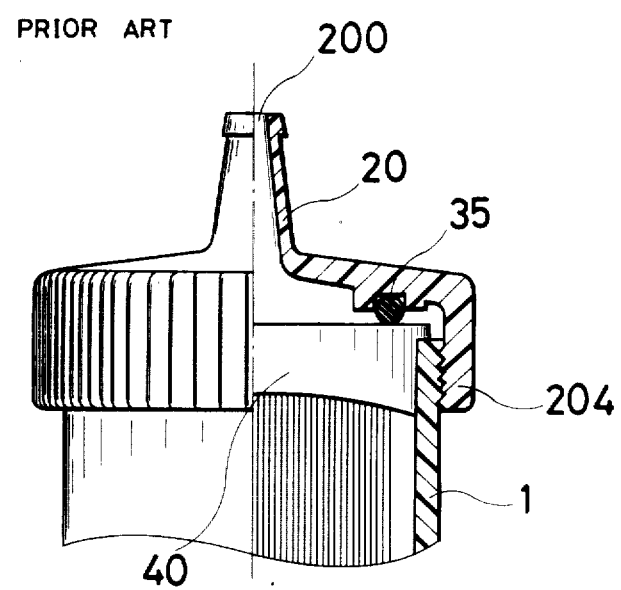

In the illustrated embodiments, the flowpath forming member 21 (25) is threadably engaged to the housing end via threads 212 (252) formed in the inner surface of the attachment portion 21b. The flowpath forming member 21 may also be fixedly secured to the housing end by bonding with adhesive, heat sealing, or electronic heat sealing. Although the thread engagement is employed in the illustrated embodiments, heat sealing is preferably used to engage the flowpath forming member to the housing end and a shape modification necessary for such heat sealing will be obvious to those skilled in the art. Anyway, the flowpath forming member is desirably mounted directly to the housing end. More elements are necessary if the flowpath forming member is secured to the housing end by means of a separate cover as in the prior art header of FIG. 4.

An elastomeric annular member 71 (75) is integrally molded to the flowpath forming member 21 (25) on the inner surface. The elastomeric annular member 71 (75) is secured in pressure contact to the outside surface of the partition 41 (45) at the peripheral portion that surrounds the hollow fiber bundle, that is, where the hollow fibers 5 are absent. A fluid-tight seal is thus provided between the flowpath forming member 21 and the partition 41 (45).

The elastomeric annular member may be integrally molded to the flowpath forming member by any desired molding techniques, preferably two-color injection molding. The flowpath forming member is first injection molded and an elastomer is then injection molded to form an ring member onto the inner surface of the flowpath member such that both members are fuse welded to each other.

Another method of molding the elastomeric annular member integral to the flowpath forming member is by insert molding. The preformed elastomeric annular member 71 is placed in the cavity of an injection mold, and a resin is then injected into the cavity to form the flowpath forming member. A plurality of fine grooves (not shown) may preferably be provided on the surface of the insert to increase the contact area for tight bonding.

The thus integrally molded flowpath member/elastomeric member assembly is fixedly secured to the end of the housing 1 by thread engagement, adhesive bonding, heat sealing, and high frequency or electronic heat sealing. Among these, electronic heat sealing is most preferred since it is rather difficult to fluid-tightly mount the assembly to the housing by thread engagement due to the friction between the elastomeric annular member and the partition.

The flowpath forming members used in the material transfer apparatus of the invention may be formed of thermoplastic resins such as polypropylene, polyethylene, polycarbonate, acrylonitrile-styrene copolymers, acrylonitrile-butadiene-styrene copolymers, etc.

When the flowpath forming member and the elastomeric annular member are formed by two-color injection molding, the elastomer to form the annular member must be fuse weldable to the resin to form the flowpath forming member. Preferable combinations of the resins used for these members are listed below.

| Resin for flowpath forming member | Elastomer for annular member |
|---|---|
| polyolefin | polyolefin elastomer |
| polyolefin | SBS elastomer |
| polycarbonate | polyurethane |
| acryronitrile-styrene | polyurethane |
| polystyrene | polyurethane |

When the elastomeric annular member is joined to the flowpath forming member by insert molding, the annular member may be formed of elastomers such as isoprene rubbers, neoprene rubbers, silicone rubbers or the like. Those elastomers fuse weldable to the resin of flowpath forming member are preferred.

Next, the elastomeric annular member is described in further detail with regard to its shape and location.

The partition 41 includes the peripheral portion that surrounds the hollow fiber bundle, that is, where the hollow fibers are absent. The elastomeric annular member 71 may preferably be secured in pressure contact to the partition 41 along the peripheral portion. If the elastomeric annular member 71 contacts the partition 41 at a central portion where the hollow fibers terminate or open, those hollow fibers in the contact area are blocked at their ends so that they are no longer effectively utilized.

The contact surface of the elastomeric annular member 71 with the partition 41 may preferably conform in shape to the surface of the partition 41 because the increased contact area ensures a fluid-tight seal between the partition 41 and the flowpath forming member 21.

The inner circumferential surface 71a of the elastomeric annular member 71 to be in contact with blood may preferably be smoothly continuous from the inner surface of the flowpath forming member 21. The smooth connection between the flowpath forming member 21 and the elastomeric annular member 71 prevents of thrombus from forming at their interface, ensuring a sufficient supply of blood to the hollow fibers near the periphery of the partition 41.

The elastomeric annular member 71 may either have a narrow cross section as shown in FIG. 3 or the wide configuration of FIGS. 1 and 2.

More illustratively, the elastomeric annular member 71 is joined to the flowpath forming member 21 at the internal corner 21c between the intermediate portion 21a and the attachment portion 21b in the embodiment of FIG. 2. Such a full contact configuration imparts a larger contact area than that available in FIG. 3 between the flowpath forming member 21 and the elastomeric annular member 71, and prevents the elastomeric annular member 21 from moving aside from the flowpath forming member to form a gap therebetween. A consistent fluid-tight seal is thus achieved between the flowpath forming member 21 and the partition 41.

The elastomeric annular member 71 of FIG. 3 has a narrower cross section than that shown in FIGS. 1 and 2, and an annular space is defined between the elastomeric annular member 71 and the attachment portion of the flowpath forming member 21. Despite its narrow contact area, the elastomeric annular member 71 is allowed to deform when it is secured in pressure contact to the partition 41 by the flowpath forming member 21. A consistent fluid-tight seal is thus achieved between the flowpath forming member 21 and the partition 41.

Although the material transfer apparatus of the invention has been described with respect to a dialyzer, the present material transfer apparatus may also be applied to an oxygenator.

The hollow fibers 5 used for the oxygenator may be formed of a polyolefin, optionally coated with silicone.

A blood and a gas such as oxygen may respectively flow through first and second fluid chambers or vice versa so that material transfer may take place in the form of gas exchange across the hollow fiber membranes 5. When the blood flows through the first fluid chamber 6 defined by the outer wall of the hollow fibers 5, the inner surface of the partitions 41, 45 and the inner wall of the housing 1, the flowpath forming member may not necessarily be provided on the gas outlet side and the gas coming out of the hollow fibers 5 may be directly released at the partition into the atmosphere.

EFFECTS OF THE INVENTION

In the material transfer apparatus of the present invention, a fluid-tight seal is provided between the flowpath forming member and the partition by the elastomeric annular member which is integrally molded to the flowpath forming member at its inner surface and brought in pressure contact with the partition. Fluid leakage due to slipping out of an O-ring occurs no longer. A reliable fluid-tight seal is thus maintained in the material transfer apparatus of the invention.

The material transfer apparatus of the invention has another advantage of ease of assembly.

What is claimed is:

1. A material transfer apparatus of hollow fiber type for transferring a certain material between first and second fluids, comprising
   a tubular housing,
   a bundle of a plurality of hollow fiber membranes axially extending through the housing and allowing the material to migrate thereacross,
   a first fluid chamber defined by the outer surface of said hollow fibers and the inner surface of said housing,
   a first fluid inlet and a first fluid outlet both provided on the housing in fluid communication with said first fluid chamber for passing the first material transfer fluid into and out of the first chamber,
   partitions supporting the opposite ends of said hollow fibers and isolating the fiber ends from said first fluid chamber,
   a second fluid inlet and a second fluid outlet both in fluid communication with the interior space of said hollow fibers for passing the second material transfer fluid into and out of the fiber interior space,
   a first flowpath forming member having the second fluid inlet mounted on one end of the housing,
   a second flowpath forming member having the second fluid outlet mounted on the other end of the housing, and
   an elastomeric annular member integrally molded to each said flowpath forming member on its inner surface, wherein the elastomeric member is secured in pressure contact to the partition by the flowpath forming member to provide a fluid-tight seal between the partition and the flowpath forming member.

2. The material transfer apparatus of claim 1 wherein the elastomeric annular member is in contact with a peripheral portion of the partition that surrounds the hollow fiber bundle.

3. The material transfer apparatus of claim 1 wherein
   said first flowpath forming member includes a leading portion of a reduced diameter to form the second fluid inlet, an intermediate portion continuously extending and dilating from the inner surface of the fluid inlet to define a flowpath for distributing the second fluid substantially over the partition, and an attachment portion continuously extending from the intermediate portion and adapted to be attached to one end of the housing,
   a first elastomeric annular member is joined to the flowpath forming member near the boundary between the intermediate and the attachment portions,
   said second flowpath forming member includes a leading portion of a reduced diameter to form the second fluid outlet, an intermediate portion continuously extending and dilating from the inner surface of the fluid outlet to define a flowpath for collecting the second fluid, and an attachment portion continuously extending from the intermediate portion and adapted to be attached to the other end of the housing, and
   a second elastomeric annular member is joined to the flowpath forming member near the boundary between the intermediate and the attachment portions.

4. The material transfer apparatus of claim 3 wherein the elastomeric annular member is in full contact with the inner boundary surfaces of the intermediate and attachment portions of the flowpath forming member.

5. The material transfer apparatus of claim 3 wherein an annular space is defined between the elastomeric annular member and the inner surface of the attachment portion of the flowpath forming member.

6. The material transfer apparatus of claim 1 wherein the attachment portion of the flowpath forming member is electronically heat sealed to the housing end.

7. The material transfer apparatus of claim 1 wherein the flowpath forming member and the elastomeric annular member are integrally molded by two-color injection molding.

8. The material transfer apparatus of claim 1 wherein the flowpath forming member is molded from a polyolefin and the elastomeric annular member is molded from a polyolefin elastomer.

9. The material transfer apparatus of claim 1 wherein the material transfer apparatus constitutes a dialyzer.

* * * * *

UNITED STATES PATENT AND TRADEMARK OFFICE
CERTIFICATE OF CORRECTION

PATENT NO. : 4,708,796

DATED : Nov. 24, 1987

INVENTOR(S) : Masayuki YOSHIMOTO, Toshiaki TAKAGI

It is certified that error appears in the above-identified patent and that said Letters Patent is hereby corrected as shown below:

IN THE ABSTRACT:

Line 2, before "tubular" insert --a--.

IN THE SPECIFICATION:

Column 3, line 61, after "illustrated" delete --.--.

Signed and Sealed this

Fourteenth Day of June, 198

Attest:

DONALD J. QUIGG

Attesting Officer

Commissioner of Patents and Trademarks